United States Patent
yang et al.

(10) Patent No.: US 11,400,440 B2
(45) Date of Patent: Aug. 2, 2022

(54) CATALYST AND PRECURSOR THEREOF AND METHOD OF FORMING DIALKYL CARBONATE

(71) Applicant: INDUSTRIAL TECHNOLOGY RESEARCH INSTITUTE, Hsinchu (TW)

(72) Inventors: Chih-Yao yang, Hsinchu (TW); Kuo-Ching Wu, Lieyu Township (TW); Hsi-Yen Hsu, Hsinchu (TW); Yu-Shan Chao, Hsinchu (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 181 days.

(21) Appl. No.: 16/727,483

(22) Filed: Dec. 26, 2019

(65) Prior Publication Data

US 2021/0178374 A1    Jun. 17, 2021

(30) Foreign Application Priority Data

Dec. 16, 2019  (TW) ................. 108145962

(51) Int. Cl.
*C07B 61/00* (2006.01)
*B01J 31/12* (2006.01)
*C07C 68/01* (2020.01)
*C07C 68/04* (2006.01)

(52) U.S. Cl.
CPC ............ *B01J 31/122* (2013.01); *C07C 68/01* (2020.01); *C07C 68/04* (2013.01); *B01J 2231/321* (2013.01); *B01J 2523/43* (2013.01); *B01J 2523/47* (2013.01); *C07C 2531/12* (2013.01)

(58) Field of Classification Search
None
See application file for complete search history.

(56) References Cited

U.S. PATENT DOCUMENTS

| | | |
|---|---|---|
| 6,346,638 B1 | 2/2002 | Tojo et al. |
| 7,435,842 B2 | 10/2008 | Miyake et al. |
| 7,541,482 B2 | 6/2009 | Miyake et al. |
| 7,842,828 B2 | 11/2010 | Bijanto et al. |
| 8,008,518 B2 | 8/2011 | Shinohata et al. |
| 8,362,289 B2 | 1/2013 | Miyake et al. |
| 9,765,013 B2 | 9/2017 | Lee et al. |
| 2007/0106050 A1 | 5/2007 | Sokolowski et al. |
| 2011/0196167 A1 | 8/2011 | Almusaiteer et al. |
| 2011/0288309 A1 | 11/2011 | Nowlan et al. |

FOREIGN PATENT DOCUMENTS

| | | |
|---|---|---|
| CN | 1938356 A | 3/2007 |
| CN | 101143322 A | 3/2008 |
| CN | 101381592 A | 3/2009 |
| CN | 101632932 A | 1/2010 |
| CN | 101947425 A | 1/2011 |
| CN | 101611077 B | 4/2012 |
| CN | 102423707 A | 4/2012 |
| CN | 102659601 A | 9/2012 |
| CN | 103044491 A | 4/2013 |
| CN | 104841414 A | 8/2015 |
| JP | 2009-242306 A | 10/2009 |
| JP | 2010-77113 A | 4/2010 |
| JP | 2011-51904 A | 3/2011 |
| JP | 2012-162523 A | 8/2012 |
| JP | 6184049 B2 | 8/2017 |
| TW | I654178 B | 3/2018 |
| WO | WO 2013/175510 A1 | 11/2013 |

OTHER PUBLICATIONS

Indian Journal of Chemistry, 46A, 854-858 (Year: 2008).*
Taiwanese Office Action and Search Report for Taiwanese Application No. 108145962, dated Oct. 26, 2020.

* cited by examiner

*Primary Examiner* — Yun Qian
(74) *Attorney, Agent, or Firm* — Birch, Stewart, Kolasch & Birch, LLP

(57) ABSTRACT

A method of forming dialkyl carbonate is provided, which includes introducing carbon dioxide into a catalyst to form dialkyl carbonate, wherein the catalyst is formed by activating a catalyst precursor using alcohol, wherein alcohol is $R^3$—OH, and $R^3$ is $C_{1-12}$ alkyl group or $C_{5-12}$ aryl or heteroaryl group. The catalyst precursor is formed by reacting $Sn(R_1)_2(L)_2$ and $Ti(OR^2)_4$, and $Sn(R^1)_2(L)_2$ and $Ti(OR^2)_4$ have a molar ratio of 1:2 to 2:1. $R^1$ is $C_{1-10}$ alkyl group, $R^2$ is H or $C_{1-12}$ alkyl group, and L is O—(C=O)—$R^5$, and $R^5$ is $C_{1-12}$ alkyl group. The dialkyl carbonate is

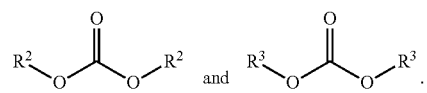

5 Claims, No Drawings

CATALYST AND PRECURSOR THEREOF AND METHOD OF FORMING DIALKYL CARBONATE

CROSS REFERENCE TO RELATED APPLICATIONS

The present application is based on, and claims priority from, Taiwan Application Serial Number 108145962, filed on Dec. 16, 2019, the disclosure of which is hereby incorporated by reference herein in its entirety.

TECHNICAL FIELD

The technical field relates to a catalyst, and in particular it relates to a catalyst that converts carbon dioxide into dialkyl carbonate.

BACKGROUND $CO_2$ is a colorless and odorless gas, which is one of the main gases that cause the greenhouse effect. $CO_2$ mainly comes from the combustion of a large number of carbon-containing fuels, including coal, oil, and natural gas. It is estimated that by 2100, the $CO_2$ content in the atmosphere will reach 500-1000 μL/L, which will cause the global average temperature to rise by 5.2° C., induce sea-level rise, and increase ocean acidity by 150%. The formulation of the "Kyoto Protocol" has clearly stipulated (legally binding) greenhouse gas quantified emission reduction targets for developed countries, and more than 100 representatives from the COP21 Paris summit voluntary signed $CO_2$ reduction targets. The emission reduction situation is very grim. The chemical utilization of $CO_2$ is converting $CO_2$ into bulk basic chemicals, organic fuels, or directly solidified as polymer materials. At present, industrialized $CO_2$ chemical utilization processes include synthesizing urea, salicylic acid, organic carbonates, inorganic carbonates, and the like.

In the process of converting $CO_2$ into chemicals, dialkyl carbonate (DRC) compound is directly synthesized by different alkyl alcohols with $CO_2$ (serving as a carbon source). The above synthesis is catalyzed by a catalyst to directly react to form the dialkyl carbonate. The method may produce dimethyl carbonate (DMC), diethyl carbonate (DEC), dihexyl carbonate (DHC), diphenyl carbonate (DPC), and other applicable dialkyl carbonate compounds. The DRC product can be (1) raw material of polycarbonate diol (PCDL) for preparing polyurethane (PU) and thermoplastic polyurethane (TPU) plastics, (2) serving as a reagent for methylation, ethylation, or carbonylation to produce chemicals such as polycarbonate (PC), isocyanate, polyurethane, and the like, (3) serving as non-toxic green solvent in paint, synthesis, and clean, due to its low viscosity, low dielectric constant, high surface tension, and excellent solubility for most of organics, (4) additive for petroleum, (5) electrolyte in lithium batteries, (6) auxiliary for cosmetic and personal care (e.g. dioctyl carbonate is mainly used as novel emollient for skin to feel dry and clean). Accordingly, a novel catalyst system is called for to directly convert carbon dioxide to diallyl carbonate.

SUMMARY

One embodiment of the disclosure provides a catalyst precursor, being formed by reacting $Sn(R^1)_2(L)_2$ and $Ti(OR^2)_4$, wherein $Sn(R^1)_2(L)_2$ and $Ti(OR^2)_4$ have a molar ratio of 1:2 to 2:1, $R^1$ is $C_{1-10}$ alkyl group, $R^2$ is H or $C_{1-12}$ alkyl group, and L is $O—(C=O)—R^5$, and $R^5$ is $C_{1-12}$ alkyl group.

In some embodiments, $Sn(R^1)_2(L)_2$ and $Ti(OR^2)_4$ have a molar ratio of 1:1, and the catalyst precursor has a chemical structure of

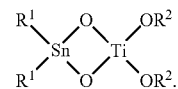

In some embodiments, $Sn(R^1)_2(L)_2$ and $Ti(OR^2)_4$ have a molar ratio of 2:1, and the catalyst precursor has a chemical structure of

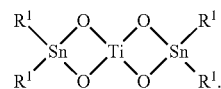

In some embodiments, $Sn(R^1)_2(L)_2$ and $Ti(OR^2)_4$ have a molar ratio of 1:2, and the catalyst precursor has a chemical structure of

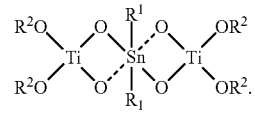

One embodiment of the disclosure provides a catalyst, which is formed by activating a catalyst precursor using alcohol, wherein the alcohol is $R^3$—OH, and $R^3$ is $C_{1-12}$ alkyl group or $C_{5-12}$ aryl or heteroaryl group, wherein the catalyst precursor is formed by reacting $Sn(R^1)_2(L)_2$ and $Ti(OR^2)_4$, and $Sn(R^1)_2(L)_2$ and $Ti(OR^2)_4$ have a molar ratio of 1:2 to 2:1, $R^1$ is $C_{1-10}$ alkyl group, $R^2$ is H or $C_{1-12}$ alkyl group, and L is $O—(C=O)—R^5$, and $R^5$ is $C_{1-12}$ alkyl group.

In some embodiments, the catalyst precursor and the alcohol have a molar ratio of 1:2 to 1:50.

In some embodiments, $Sn(R^1)_2(L)_2$ and $Ti(OR^2)_4$ have a molar ratio of 1:1, and the catalyst precursor has a chemical structure of

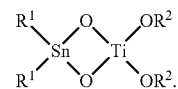

In some embodiments, $Sn(R^1)_2(L)_2$ and $Ti(OR^2)_4$ have a molar ratio of 2:1, and the catalyst precursor has a chemical structure of

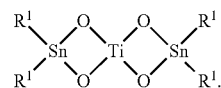

In some embodiments, $Sn(R^1)_2(L)_2$ and $Ti(OR^2)_4$ have a molar ratio of 1:2, and the catalyst precursor has a chemical structure of

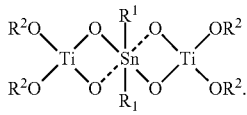

One embodiment of the disclosure provides a method of forming dialkyl carbonate, including: introducing carbon dioxide into a catalyst to form dialkyl carbonate, wherein the catalyst is formed by activating a catalyst precursor using alcohol, wherein the alcohol is $R^3$—OH, and $R^3$ is $C_{1-12}$ alkyl group or $C_{5-12}$ aryl or heteroaryl group, wherein the catalyst precursor is formed by reacting $Sn(R^1)_2(L)_2$ and $Ti(OR^2)_4$, and $Sn(R^1)_2(L)_2$ and $Ti(OR^2)_4$ have a molar ratio of 1:2 to 2:1, le is $C_{1-10}$ alkyl group, $R^2$ is H or $C_{1-12}$ alkyl group, and L is O—(C=O)—$R^5$, and $R^5$ is $C_{1-12}$ alkyl group, wherein the dialkyl carbonate is

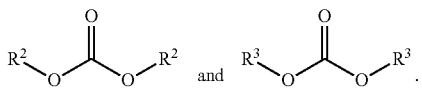

In some embodiments, the step of introducing carbon dioxide into the catalyst is performed at a temperature of 80° C. to 160° C.

In some embodiments, the step of introducing carbon dioxide into the catalyst is performed under a pressure of 20 bar to 80 bar.

In some embodiments, $Sn(R^1)_2(L)_2$ and $Ti(OR^2)_4$ have a molar ratio of 1:1, and the catalyst precursor has a chemical structure of

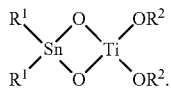

In some embodiments, $Sn(R^1)_2(L)_2$ and $Ti(OR^2)_4$ have a molar ratio of 2:1, and the catalyst precursor has a chemical structure of

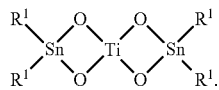

In some embodiments, $Sn(R^1)_2(L)_2$ and $Ti(OR^2)_4$ have a molar ratio of 1:2, and the catalyst precursor has a chemical structure of

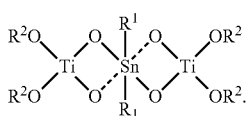

In some embodiments, the method further includes activating the used catalyst using another alcohol to form a re-activated catalyst after forming the dialkyl carbonate, wherein the other alcohol is $R^4$—OH, and $R^4$ is $C_{1-12}$ alkyl group or $C_{5-12}$ aryl or heteroaryl group.

In some embodiments, the method further includes introducing carbon dioxide to the re-activated catalyst to form dialkyl carbonate.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

One embodiment of the disclosure provides a catalyst precursor, being formed by reacting $Sn(R^1)_2(L)_2$ and $Ti(OR^2)_4$, $R^1$ is $C_{1-10}$ alkyl group, $R^2$ is H or $C_{1-12}$ alkyl group, and L is O—(C=O)—$R^5$, and $R^5$ is $C_{1-12}$ alkyl group. In one embodiment, $Sn(R^1)_2(L)_2$ and $Ti(OR^2)_4$ have a molar ratio of 1:2 to 2:1. If $Sn(R^1)_2(L)_2$ ratio is too high or too low, the catalyst formed by activating the catalyst precursor cannot efficiently convert carbon dioxide to dialkyl carbonate. For example, $Sn(R^1)_2(L)_2$ and $Ti(OR^2)_4$ can be heated to a temperature of 120° C. to 220° C. under an atmosphere pressure for a period of 1 hour to 10 hours to form the catalyst precursor. If the reaction temperature is too low or the reaction period is too short, the yield of the catalyst precursor will be too low. If the reaction temperature is too high or the reaction period is too long, the catalyst precursor will gradually crack and resemble to loss activity.

In one embodiment, $Sn(R^1)_2(L)_2$ and $Ti(OR^2)_4$ have a molar ratio of 1:1, and the catalyst precursor has a chemical structure of

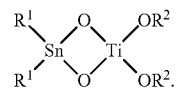

In one embodiment, $Sn(R^1)_2(L)_2$ and $Ti(OR^2)_4$ have a molar ratio of 2:1, and the catalyst precursor has a chemical structure of

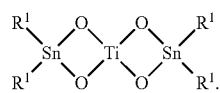

In one embodiment, $Sn(R^1)_2(L)_2$ and $Ti(OR^2)_4$ have a molar ratio of 1:2, and the catalyst precursor has a chemical structure of

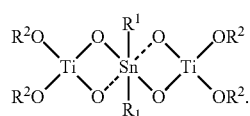

It should be understood that if $Sn(R^1)_2(L)_2$ and $Ti(OR^2)_4$ have other molar ratios, the catalyst precursor may have different proportions of the combination of the above three chemical structures.

One embodiment of the disclosure provides a catalyst being formed by activating the described catalyst precursor using alcohol. The catalyst precursor is similar to the one described above, and so it is not described again in detail here. The alcohol for activating the catalyst precursor is $R^3$—OH, and $R^3$ is $C_{1-12}$ alkyl group or $C_{5-12}$ aryl or heteroaryl group. In one embodiment, the catalyst precursor and the alcohol have a molar ratio of 1:2 to 1:50. If the alcohol ratio is too low, the amount of the catalyst precursor that is activated will be too low to further synthesize dialkyl carbonate. If the alcohol ratio is too high, the reflux and recycling of alcohol consumes too much energy. In one embodiment, the step of activating the catalyst precursor is performed at a pressure of 1 bar to 30 bar for a temperature of 120° C. to 220° C. for a period of 1 hour to 10 hours. If the activation pressure is too high, the moisture generated from the activation will be not easily removed, the activated catalyst ratio will be lowered, and synthesis of dialkyl carbonate will be unfavorable. If the activation temperature is too low, the activated catalyst ratio will be too low, the reaction rate will be lowered, and the synthesis of dialkyl carbonate will be unfavorable. If the activation temperature is too high, the catalyst will gradually crack and resemble to loss activity. If the activation period is too short, the activated catalyst ratio will be too low. If the activation period is too long, the catalyst will easily crack and resemble to loss activity.

One embodiment of the disclosure provides a method of forming dialkyl carbonate, including introducing carbon dioxide into the described catalyst to form dialkyl carbonate. The catalyst precursor is similar to the one described above, and so it is not described again in detail here. In one embodiment, the dialkyl carbonate is

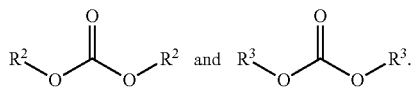

It should be understood that if $R^3$ of the alcohol $R^3$—OH for activating the catalyst precursor is the same as $R^2$ of the $Ti(OR^2)_4$ for forming the catalyst precursor, (e.g. both are butyl group), the dialkyl carbonate will be a single product. For example, the dialkyl carbonate can be dimethyl carbonate (DMC), diethyl carbonate (DEC), dibutyl carbonate (DBC), dihexyl carbonate (DHC), or diphenyl carbonate (DPC). If $R^3$ of the alcohol $R^3$—OH for activating the catalyst precursor is different from $R^2$ of the $Ti(OR^2)_4$ for forming the catalyst precursor, (e.g. $R^3$ is butyl group and $R^2$ is hexyl group), the alky groups of two sides on the dialkyl carbonate will be the same (e.g. dibutyl carbonate (DBC) and dihexyl carbonate (DHC)) rather than different (e.g. butyl hexyl carbonate).

In one embodiment, the step of introducing the carbon dioxide into the catalyst is performed at a temperature of 80° C. to 160° C. If the temperature is too low, the conversion rate of $CO_2$ adsorbed on the catalyst will be lowered. If the temperature is too high, two shortcomings may occur: (1) the desorption amount of the $CO_2$ on the catalyst will be increased to lower the yield of the dialkyl carbonate, and (2) the catalyst will be easily degraded and the esterification will be unfavorable. In one embodiment, the step of introducing the carbon dioxide into the catalyst is performed at a pressure of 20 bar to 80 bar. If the pressure is too low, the adsorption amount of the $CO_2$ on the catalyst will be lowered to lower the yield of the dialkyl carbonate. If the pressure is too high, the adsorption amount of the $CO_2$ on the catalyst will be increased to enhance the yield of the dialkyl carbonate. However, the reaction system should be high pressure resistant, which may increase the entire equipment cost.

In one embodiment, the method of forming dialkyl carbonate further includes re-activating the used catalyst to form a re-activated catalyst using another alcohol after forming the dialkyl carbonate. The other alcohol is $R^4$—OH, and $R^4$ is $C_{1-12}$ alkyl group of $C_{5-12}$ aryl group or heteroaryl group. It should be understood that the other $R^4$—OH can be the same as or different from the previous alcohol $R^3$—OH used for activating the catalyst precursor.

In one embodiment, the method of forming dialkyl carbonate further includes introducing carbon dioxide into the re-activated catalyst to form dialkyl carbonate. It should be understood that the step of activating the used catalyst using alcohol, and introducing carbon dioxide into the re-activated catalyst to form the dialkyl carbonate, can be repeated. In one embodiment, the step of re-activating catalyst and introducing the carbon dioxide into the re-activated catalyst can be repeated tens or even hundreds of times.

Below, exemplary embodiments will be described in detail so as to be easily realized by a person having ordinary knowledge in the art. The inventive concept may be embodied in various forms without being limited to the exemplary embodiments set forth herein.

EXAMPLES

Example 1

56.2 g of dibutyl tin diacetate (0.16 mole) and 54.4 g of tetrabutyl orthotitanate (0.16 mole) were mixed, and then heated to 190° C. to react for 1 hour, thereby distilling out 36.4 g of butyl acetate to obtain 68.9 g of tin-titanium catalyst precursor. The reaction is shown below, and the chemical structure of the tin-titanium catalyst precursor could be determined by Sn-NMR and mass spectroscopy.

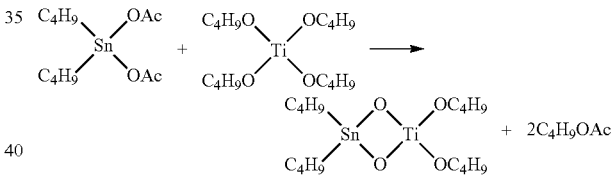

68.9 g of the tin-titanium catalyst precursor and 111 g of butanol (having a molar ratio of about 1:10) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by gas chromatography (GC), in which the yield of dibutyl carbonate (DBC) was about 17.7%. The yield was defined as the DBC mole divided by the catalyst mole (e.g. DBC mole/catalyst mole).

Example 2

35.1 g of dibutyl tin diacetate (0.1 mole) and 34 g of tetrabutyl orthotitanate (0.1 mole) were mixed, and then heated to 190° C. to react for 1 hour, thereby distilling out 22.7 g of butyl acetate to obtain 41.4 g of tin-titanium catalyst precursor. The reaction was similar to that in Example 1. 41.4 g of the tin-titanium catalyst precursor and 238 g of butanol (having a molar ratio of about 1:35) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 22.7%.

Example 3

31.6 g of dibutyl tin diacetate (0.09 mole) and 45.9 g of tetrabutyl orthotitanate (0.14 mole) were mixed, and then heated to 190° C. to react for 1 hour, thereby distilling out 19.1 g of butyl acetate to obtain 55.3 g of tin-titanium catalyst precursor. 55.3 g of the tin-titanium catalyst precursor and 239 g of butanol (having a molar ratio of about 1:35) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 25.7%.

Example 4

70.2 g of dibutyl tin diacetate (0.2 mole) and 68 g of tetrabutyl orthotitanate (0.2 mole) were mixed, and then heated to 190° C. to react for 1 hour, thereby distilling out 47.8 g of butyl acetate to obtain 90.5 g of tin-titanium catalyst precursor. 90.5 g of the tin-titanium catalyst precursor and 204 g of hexanol (having a molar ratio of about 1:35) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the hexanol to obtain catalyst. The butanol and hexanol containing water were removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 10.85%, and the yield of dihexyl carbonate (DHC) was about 16.52%.

Example 5

The DBC and the used catalyst in Example 1 were separated to each other, and the used catalyst and 111 g of butanol (having a molar ratio of about 1:10) were added to an autoclave. The nitrogen pressure in the autoclave was increased to 7 atm. The mixture of the used catalyst and the butanol was reacted at 170° C. for a period of 1 hour, thereby re-activating the used catalyst by the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 21.17%.

Example 6

105.3 g of dibutyl tin diacetate (0.3 mole) and 68 g of tetrabutyl orthotitanate (0.2 mole) were mixed, and then heated to 190° C. to react for 1 hour, thereby distilling out 25.1 g of butyl acetate to obtain 145.2 g of tin-titanium catalyst precursor. 145.2 g of the tin-titanium catalyst precursor and 120 g of butanol (having a molar ratio of about 1:35) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 17.2%.

Comparative Example 1

250 g of dibutyl tin oxide (1 mole), 296 g of butanol (4 mole), and 50 g of toluene were stirred, and then heated to 110° C. to distill out the toluene and water. After the toluene was completely removed, the mixture was heated to 160° C. to remove the butanol. Subsequently, 125.6 g of pale yellow liquid (catalyst precursor) and 148 g of butanol (having a molar ratio of about 1:10) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 13.36%.

Comparative Example 2

210.6 g of dibutyl tin diacetate (0.6 mole) and 68 g of tetrabutyl orthotitanate (0.2 mole) were mixed, and then heated to 190° C. to react for 1 hour, thereby distilling out 38.3 g of butyl acetate to obtain 237.1 g of tin-titanium catalyst precursor. 237.1 g of the tin-titanium catalyst precursor and 520 g of butanol (having a molar ratio of about 1:35) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 10.2%.

Comparative Example 3

631.8 g of dibutyl tin diacetate (1.8 mole) and 68 g of tetrabutyl orthotitanate (0.2 mole) were mixed, and then heated to 190° C. to react for 1 hour, thereby distilling out 40.2 g of butyl acetate to obtain 642.6 g of tin-titanium catalyst precursor. 642.6 g of the tin-titanium catalyst precursor and 1400 g of butanol (having a molar ratio of about 1:35) were added to an autoclave. The air in the autoclave was cleaned out by nitrogen, and the pressure in the autoclave was increased to 7 atm. The mixture of the tin-titanium catalyst precursor and the butanol was reacted at 170° C. for a period of 1 hour, thereby activating the tin-titanium catalyst precursor using the butanol to obtain catalyst. The butanol containing water was removed from the autoclave, and the temperature of the catalyst returned to room temperature. Subsequently, 40 bar of carbon dioxide was introduced into the catalyst in the autoclave to react at a temperature of 120° C. for a period of 4 hours. The reaction result was quantitatively analyzed by GC, in which the yield of DBC was about 2.11%.

Comparative Example 4

70.2 g of dibutyl tin diacetate (0.2 mole), 68 g of tetrabutyl orthotitanate (0.2 mole), and 518 g of butanol (7 mole), having a molar ratio of about 1:1:35, were added to an autoclave. Subsequently, 40 bar of carbon dioxide was introduced into the mixture in the autoclave to react at a temperature of 120° C. for a period of 4 hours. The reaction result was quantitatively analyzed by GC, in which the yield of DBC was about 0%.

Comparative Example 5

56.2 g of dibutyl tin diacetate (0.16 mole) and 54.4 g of tetrabutyl orthotitanate (0.16 mole) were mixed, and then heated to 190° C. to react for 1 hour, thereby distilling out 36.4 g of butyl acetate to obtain 68.9 g of tin-titanium catalyst precursor. 68.9 g of the tin-titanium catalyst precursor was added to an autoclave. Subsequently, 40 bar of carbon dioxide was introduced into the tin-titanium catalyst precursor in the autoclave to react at a temperature of 120° C. for a period of 4 hours. The reaction result was quantitatively analyzed by GC, in which the yield of DBC was about 3.36%.

TABLE 1

| Serial No. | Sn:Ti:alcohol (molar ratio) | Yield |
| --- | --- | --- |
| Example 1 | 1:1:10 (butanol) | DBC: 17.70 % |
| Example 2 | 1:1:35 (butanol) | DBC: 22.70 % |
| Example 3 | 1:1.5:35 (butanol) | DBC: 25.70 % |

TABLE 1-continued

| Serial No. | Sn:Ti:alcohol (molar ratio) | Yield |
| --- | --- | --- |
| Example 4 | 1:1:35 (hexanol) | DBC: 10.85 % |
| | | DHC: 16.52 % |
| Example 5 | 1 (the used catalyst from Example 1 being re-activated):10 (butanol) | DBC: 21.17 % |
| Example 6 | 1.5:1:35 (butanol) | DBC: 17.20 % |
| Comparative Example 1 | 1 (dibutyl dibutoxy tin catalyst):0:10 (butanol) | DBC: 13.36 % |
| Comparative Example 2 | 3:1:35 (butanol) | DBC: 10.2 % |
| Comparative Example 3 | 9:1:35 (butanol) | DBC: 2.11 % |
| Comparative Example 4 | 1:1:35 (only mixing) | DBC: 0% |
| Comparative Example 5 | 1:1:0 (no activation) | DBC: 3.36% |

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A method of forming dialkyl carbonate, comprising:
introducing carbon dioxide into a catalyst to form dialkyl carbonate,
wherein the catalyst is formed by activating a catalyst precursor using alcohol,
wherein the alcohol is $R^3$—OH, and $R^3$ is $C_{1-12}$ alkyl group,
wherein the catalyst precursor has a chemical structure of

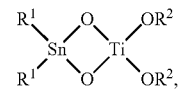

$R^1$ is butyl group, and
$R^2$ is $C_{4-6}$ alkyl group,
wherein the dialkyl carbonate is

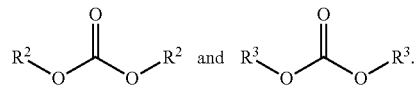

2. The method as claimed in claim 1, wherein the step of introducing carbon dioxide into the catalyst is performed at a temperature of 80° C. to 160° C.

3. The method as claimed in claim 1, wherein the step of introducing carbon dioxide into the catalyst is performed under a pressure of 20 bar to 80 bar.

4. The method as claimed in claim 1, further comprising activating the used catalyst using another alcohol to form a re-activated catalyst after forming the dialkyl carbonate, wherein the other alcohol is $R^4$—OH, and $R^4$ is $C_{1-12}$ alkyl group.

5. The method as claimed in claim 4, further comprising introducing carbon dioxide to the re-activated catalyst to form dialkyl carbonate.

* * * * *